United States Patent [19] — Kanno et al.

[11] 4,130,464

[45] Dec. 19, 1978

[54] METHOD OF EVALUATING THE CORROSION RATES OF METALS

[75] Inventors: Kenichi Kanno; Masayuki Suzuki, both of Yokohama; Yuichi Sato, Atsugi, all of Japan

[73] Assignee: Tokyo Shibaura Electric Co., Ltd., Kawasaki, Japan

[21] Appl. No.: 798,168

[22] Filed: May 18, 1977

[30] Foreign Application Priority Data

May 18, 1976 [JP] Japan .................................. 51-56076

Oct. 22, 1976 [JP] Japan .................................. 51-127016

[51] Int. Cl.[2] ...................... G01N 27/46; G01N 27/30

[52] U.S. Cl. .................................. 204/1 T; 204/195 C

[58] Field of Search ............................ 204/1 C, 195 C

[56] References Cited

U.S. PATENT DOCUMENTS 3,616,417 10/1971 Wilson ............................ 204/195 C

OTHER PUBLICATIONS

M. Prazak, "The Polarization Resistance Method for Corrosion Testing", *Werkstoffe und Korrosion*, pp. 104–112 (1974).

"Techniques of Electrochemistry", vol. 1, Edited by E. Yeager et al., Wiley-Interscience, New York (1972), pp. 229-232.

I. Fried, "The Chemistry of Electrode Processes", Academic Press, New York (1973), pp. 151-152.

"Corrosion", vol. 2, Edited by L. L. Shreir, Newnes-Butterworths, London (1976), pp. 20-35 to 20-40.

P. J. Aragon et al., "Use of Charge Curve Analysis Technique for In-Vivo Determination of Corrosion Rates", *Corrosion*, vol. 30, pp. 432-436 (1974).

*Primary Examiner*—John H. Mack

*Assistant Examiner*—Aaron Weisstuch

*Attorney, Agent, or Firm*—Oblon, Fisher, Spivak, McClelland & Maier

[57] ABSTRACT

A test piece of metal with a given area S is disposed with a reference electrode in test solution. The open circuit potential $E_{cor}$, i.e. the corrosion potential, of the test piece is measured as the reference electrode potential. A given amount of charges q from a capacitor is instantaneously fed through the reference electrode to the electrical double layer of the test piece. When that a given amount of charge q is stored in the electrical double layer, the absolute value of polarization potential of the test piece sharply increases. Then, the absolute value of the polarization potential gradually decreases due to the corrosion reaction. The polarization potential variation is recorded referred to the reference electrode as a polarization potential ($\eta_t$) − time (t) curve by a potential recorder with an extremely high input impedance. The measurement result of the polarization potential ($\eta_t$) − time (t) curve may be theoretically expressed by the equation $\log \eta_t = -t/(C_D R_p) + \log \eta_0$. Therefore, the initial polarization potential $\eta_0$ may be obtained by extrapolating the measurement result to the initial time t=0. The differential capacitance of the double layer $C_D$ can readily be calculated by the equation $q/S = \Delta q = C_D \eta_0$, and thus the polarization resistance $R_p$ is obtained from the measurement result. Since the polarization resistance $R_p$ is inversely proportional to the corrosion rate, the corrosion rate may be evaluated. The corrosion rate also is obtained from the polarization resistance $R_p$ by using a theoretical equation.

6 Claims, 9 Drawing Figures

18 20 22 12 24 26 28 16 30 34 32 14-1 14-2 14-3 14-4 14 36 2 4 6 38 48 42 49 46 44

POTENTIAL DIFFERENCE RECORDER 40

PULSE GENERATOR 8
2
4
6
POTENTIAL DIFFERENCE RECORDER 10

Rs
Cd
Rp 18
20
22
12
24
26
28
30
16
2
4
6
32
34
36
V
14-1
14-2
14-3
14-4
14
38
42
48
46
49
44
POTENTIAL DIFFERENCE RECORDER 40

ηt (mv)
t (sec)

log ηt
t (sec)

POTENTIAL DIFFERENCE RECORDER 10
52
50
2
6
PULSE GENERATOR 8

18
24
48
46
42
44
12
20
22
26
28
16
49
6
2
30
32
34
52
POTENTIAL DIFFERENCE RECORDER 40
14-1
14-2
14-3
14-4
V
36
50
38
62
60
56
58
14
54

METHOD OF EVALUATING THE CORROSION RATES OF METALS

BACKGROUND OF THE INVENTION

The present invention relates to a coulostatic method of evaluating the corrosion rates of metal and a measuring apparatus used for same.

The weight loss method has been long known for evaluating the corrosion rates of metal. This direct method is able to measure the corrosion rate of a metal surely and accurately, but it requires a long time to obtain the measurement result and fails to obtain the corrosion rate change with respect to time.

Recently, the polarization resistance method has been used for electrochemical evaluation of the corrosion rates of metal. The polarization resistance method is disclosed in "J. Electrochem. Soc., 104,56 (1957)" by M. Stern & A. Geary, "Corrosion, 14, 440t (1958)" by M. Stern, and "Proc. Am. Soc. Testing Materials, 59, 1280 (1959)" by M. Stern & E. Weisert. This method is based on the fact that corrosion of a metal involves an electrode reaction where metal ions are dissolved from the metal surface and the rate of the electrode reaction relates to the value of the current flowing in a corrosion reaction. In this method, a metal test piece having a corrosion potential $E_{corr}$ in a test solution is used as a working electrode. A constant current (I) is then made to flow from the test metal piece to a counter electrode. Under this condition, the potential $E_{mes}$ is measured. From the corrosion potential $E_{corr}$ and the measured potential $E_{mes}$, the change of the potential $\eta$ is calculated by $72 = E_{mes} - E_{corr}$, and then the polarization resistance $R_p$ is obtained by the equation (1)

$$\eta = I \cdot R_p \qquad (1)$$

The corrosion rate is obtained from the relation that the polarization resistance $R_p$ calculated from the equation (1) in inversely proportional to the corrosion rate.

The polarization resistance method using constant current is rapid for obtaining the corrosion rate, compared to the weight loss method, but it still suffers from the following problems. A relatively long time must be taken until the potential $E_{mes}$ of the metal piece reaches a constant value, i.e. the potential $\eta$ reaches a constant value. A long measurement time permits a continuous current flow over the surface of the metal piece, resulting in change of the surface condition of the metal piece. This can cause an experimental errors. In the case that a solution has a large solution resistance, its large ohmic drop gives rise to measurement errors. These errors must be compensated through a complex measuring operation and calculation.

SUMMARY OF THE INVENTION

Accordingly, an object of the present invention is to provide a method of evaluating the corrosion rate of a metal in which the polarization resistance of a metal test piece is rapidly and accurately obtained and the corrosion rate is calculated from the obtained polarization resistance.

Another object of the present invention is to provide an method of evaluating the corrosion rate of a metal in which the corrosion rate is accurately obtained without any correction for the resistance of the test solution.

Still another object of the present invention is to provide a measuring apparatus for accurately and rapidly measuring the variation of polarization potential of a metal with respect to time.

In one preferred form of the present invention, a method of evaluating the corrosion rate of a metal comprises feeding a given amount of charge q to the electrical double layer of a metal test piece having a given area S and disposed in corrosion solution; measuring the value of polarization potential $\eta_t$ of said metal test piece, of which the potential sharply increases due to the application of the given amount of charge and gradually decays due to a corrosion reaction and returns to the corrosion potential, via a reference electrode disposed along with said metal test piece in a corrosion solution, said polarization potential being measured as a function of time t; and calculating the initial polarization potential $\eta_0$ at time $t = 0$ from said polarization potential $\eta_t$ measured as the function of time t, and deriving the polarization resistance $R_p$ inversely proportional to the corrosion rate from said initial polarization potential $\eta_0$ and the charge q fed to said metal test piece and the measured $\eta_t - t$ relationship; whereby the corrosion rate of the metal is evaluated with reference to said polarization resistance $R_p$.

In another preferred form of the present invention, a measuring apparatus used for the method for evaluating the corrosion rates of metal comprises a corrosion solution: a cell containing said test solution therein; a metal test piece having a given area immersed in the corrosion solution in said cell, the corrosion rate of which is to be evaluated; a reference electrode disposed along with said metal piece in said corrosion solution; means for instantaneously feeding a given amount of charge to said test metal piece through said reference electrode; and recording means for recording the potential of said metal test piece versus said reference electrode as a function of time.

Other objects and features of the present invention will be apparent upon careful consideration of the following description when taken in connection with the accompanying drawings in which:

DETAILED DESCRIPTION OF THE PREFERRED EMBODIMENTS

The method of evaluating the corrosion rate of a metal is an application of the coulostatic method. In the evaluation method, the corrosion rate is analyzed on the basis of the measurement results obtained by the measuring apparatus shown in FIG. 1. The coulostatic method proposed by P. Delahay is a measuring method concerning electrode reactions, which is discussed in detail in "J. Phys. Chem, 66, 2204 (1962)" by P. Delahay and "Ibid, 66, 2208 (1962)" by P. Delahay and A. Aramata. In short, the coulostatic method utilizes the interface between electrode and solution as serving as a sort of leaky capacitor. In this method, the electrical double layer at the interface is instantaneously charged with a given amount of charges. The electrode reaction occurring due to the charging of the double layer is recorded as the variation of electrode potential versus time. The information about the rate of the electrode reaction is calculated from the recorded data.

The present inventors have invented a method of evaluating the corrosion rate of a metal, considering the fact that corrosion is a sort of electrode reaction and that the time variation of a potential has a close relation to the corrosion rate.

Figure 1:
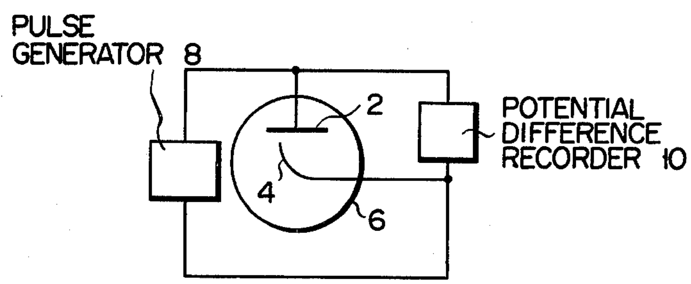
FIG. 1 illustrates in block form a measuring apparatus used for a method for evaluating the corrosion rate of a metal according to an embodiment of the invention.

Referring now to FIG. 1, there is shown an embodiment of a measuring apparatus of the invention for obtaining the variation of the polarization potential $\eta_t$ with respect to time. The measuring apparatus includes a metal test piece 2 with a given area S serving as a working electrode, such as mild steels, stainless steels, other metals and the like; a reference electrode 4 disposed facing the test metal piece 2; and a cell 6 filled with test solution such as water in which the test metal piece 2 and the reference electrode 4 are disposed. The working electrode 2 and the reference electrode 4 are connected to a pulse generator 8 and a high impedance potential recorder 10, respectively. In the measuring apparatus shown in FIG. 1, a given amount of charge in the form of pulse q from the pulse generator 8 is instantaneously applied to the electrical double layer of the metal piece 2, through the reference electrode 4. Variation of the potential $\eta_t$ of the test piece 2 as it is charged is recorded versus the reference electrode as a function of time by the potential recorder 10. A sufficiently short period is preferable for the pulse width of the pulse generated by the pulse generator 8, e.g. several μs to several ms. Preferably, the charge q of the pulse applied to the test piece 2 is of such an extent that the potential of the metal piece 2 changes only by several mV. The potential recorder 10 has an extremely high input impedance. As a result the current flowing from the metal piece 2 to the recorder 10 via the reference electrode 4 is negligibly small. This means that the polarization potential of the metal piece 2 is measured substantially through an open circuit. The potential decay $\eta_t$ of the test piece 2 arises from the corrosion reaction of test piece 2 progressing and thereby consuming the charge q charged therein. In this manner, the variation of the potential $\eta_t$ due to the corrosion reaction may be accurately measured.

The explanation to follow is for the method of evaluating the corrosion rate of a metal on the basis of the measured values provided by the apparatus shown in FIG. 1. The metal test piece 2 in the test solution is at the open-circuit potential, i.e. the corrosion potential $E_{corr}$. When the electrical double layer of the metal piece 2 is instantaneously charged with charge q and the absolute value of the potential of the metal piece 2 reaches the maximum $E_{mes}$, the initial polarization potential $\eta_0$ of the test metal piece 2 is given by the following equation $$\eta_0 = E_{mes} - E_{corr} \quad (2)$$

As will be seen later, the initial polarization potential $\eta_0$ can not be measured directly by the potential recorder 10. The reason for this is that the ohmic drop of the solution resistance $R_s$ gives rise to incorrect measurement. The variation of polarization potential $\eta_t$ with time measured by the recorder 10 is theoretically given by $$\eta_t = \eta_0 \exp(-t/C_D R_p) \quad (3)$$

The derivation of the general equation (3) will be referred to later.

The equation (3) may be rewritten into a logarithmic equation $$\log\eta_t - \log\eta_0 = -t/C_D R_p \quad (4)$$

where $C_D$ is the differential capacitance of the test piece 2 and $R_p$ is the polarization resistance of the test piece 2. Both of the values are per unit area. The differential capacitance $C_D$ may be expressed as $$C_D = \Delta q/\eta_0 \quad (5)$$

where $\Delta q = q/S$ and S is the area of the metal piece 2. The differential capacitance $C_D$ of the test piece varies with the potential value thereof, but it is considered to be substantially constant within a small voltage domain. Δq is charge density.

The polarization resistance $R_p$ may be calculated from the data measured by recorder 10 and equations (4) and (5). Equation (4) describes a rectilinear line on a semi-logarithmic graph. Accordingly, the initial potential $\eta_O$ may be obtained if the measured values of $N_t$ ust are plotted on a semi-logarithmic graph and the plotted rectilinear line is extrapolated to the initial time $t = 0$. The differential capacitance $C_D$ is obtained by substituting the initial polarization potential $\eta_O$ into the equation (5). The polarization resistance $R_p$ is obtained from the slope of the plotted line and the differential capacitance $C_D$. Generally, the polarization resistance $R_p$ is inversely proportional to the corrosion rate V. As seen from equations (6) and (7) to be described later, the corrosion rate V can readily be calculated from the polarization resistance $R_p$. By using only the resistance $R_p$, therefore, it is possible to decide whether the test metal piece is resistive to corrosion in a certain test solution or not.

Figure 2:
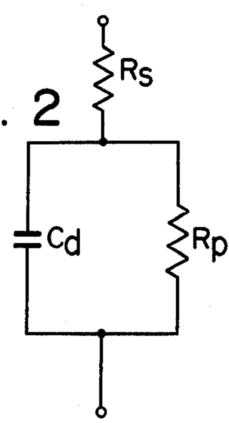
FIG. 2 illustrates the equivalent circuit of the corrosion reaction occurring in the measuring cell shown in FIG. 1.

The corrosion reaction of the metal piece 2 may be electrically expressed by the equivalent circuit shown in FIG. 2. The solution resistance $R_s$ serves as a resistor for the applied voltage when the differential capacitance $C_D$ is charged through the reference electrode 4. In the measurement of the polarization resistance $R_p$, the polarization potential $\eta_t$ is measured at substantially open circuit, and therefore the measured value undergoes no influence due to the above mentioned solution resistance $R_s$. Even if the measured value should undergo a slight influence due to the solution resistance $R_s$, the initial polarization value is obtained through extrapolation. Therefore, the obtained initial polarization value $\eta_o$ is very accurate, it undergoes no influence by the solution resistance $R_s$. From comparison of the equivalent circuit of FIG. 2 and the equation (3), it will be understood that the corrosion reaction of a metal may be electrically measured as a transient phenomenon in a closed circuit consisting of the capacitor $C_D$ and the resistor $R_p$, that is, the corrosion reaction may be expressed as a phenomena where the charge density $\Delta q$ of the charged capacitor $C_D$ is consumed in the resistor $R_p$.

The method will be described for obtaining the corrosion rate of the test piece 2 from the polarization resistance $R_p$.

Generally, the corrosion rate V is expressed $$V = (M/ZF) \cdot I_{corr} \tag{6}$$

where $I_{corr}$ is corrosion current density and given $$I_{corr} = (K/2.3)/R_p \tag{7}$$

In these equations, K is a constant inherent to the corrosion reaction, M is the atomic weight of the test piece, Z is the valence of the dissolved metal ion, and F is the Faraday constant. As seen from equations (6) and (7), the corrosion rate V is inversely proportional to the polarization resistance $R_p$ and, if the resistance $R_p$ is known, the corrosion rate is easily calculated.

The theoretical derivation of the equations (3) and (4) will be given for a better understanding of the above-mentioned equations.

The "Stern-Geary" equation disclosed in the above-mentioned literatures is expressed by the equation (8)

$$I_t = 2.3 \cdot I_{corr} \cdot \{(\beta_a + \beta_c)/\beta_a\beta_c\} \cdot \eta_t \tag{8}$$

where $\beta_a = 2.3\ RT/(n_+ \cdot \alpha_+ \cdot F)$ and $\beta_c = 2.3\ RT/(n_- \cdot \alpha_- \cdot F)$. $I_t$ is the faradaic current at time t, $\alpha+$ and $\alpha-$ the transfer coefficient of the anodic and cathodic reactions, n+ and n− the number of electrons involved in the anodic and cathodic reactions $I_{corr}$ is the corrosion current density, R, T and F the gas constant, absolute temperature and faradaic constant, respectively. We can write $\Delta q_t$, the amount of the charge density which is consumed from time O to time t by the corrosion reaction, as follows $$\Delta q_t = C_D(\eta_O - \eta_t) \tag{9}$$

The charge density $\Delta q_t$ is also expressed by the equation (8)

$$\Delta q_t = \int_0^t I_t\,dt = \int_0^t 2.3\ \{(\beta_a+\beta_c)/\beta_a\beta_c\}\eta_t \cdot I_{corr} dt \tag{10}$$

From the equations (8) and (9), the following differential equation is obtained $$-C_D \cdot \frac{d\eta_t}{dt} = 2.3\ \{(\beta_a+\beta_c)/\beta_a\beta_c\}\eta_t \cdot I_{corr} \tag{11}$$

Solving the equation (11) under the initial condition that $\eta_t = \eta_O$ at t = O, we can derive the following equation $$\eta_t = \eta_O \exp\{-2.3\ I_{corr} \cdot t/(C_D K)\} \tag{12}$$

where $K = \beta_a\beta_c/(\beta_a + \beta_c)$ and $\beta_a$ and $\beta_c$ are Tafel slopes of anodic and cathodic reaction respectively. As seen from the equation (7), $K/2.3 \cdot I_{corr}$ may be replaced by $R_p$. Using the resistance $R_p$ in place of $K/2.3 \cdot I_{corr}$ leads to the equation (3) mentioned above.

$$\eta_t = \eta_O \exp\{-t/(C_D \cdot R_p)\} \tag{3}$$

From the foregoing description, the polarization resistance $R_p$ is calculated from the slope of the plotted line and the differential capacitance $C_D$ which is calculated from the charge density $\Delta q$ and the initial polarization potential $\eta_O$ obtained by extrapolation and the corrosion rate V is calculated from polarization resistance $R_p$ so obtained.

Figure 3:
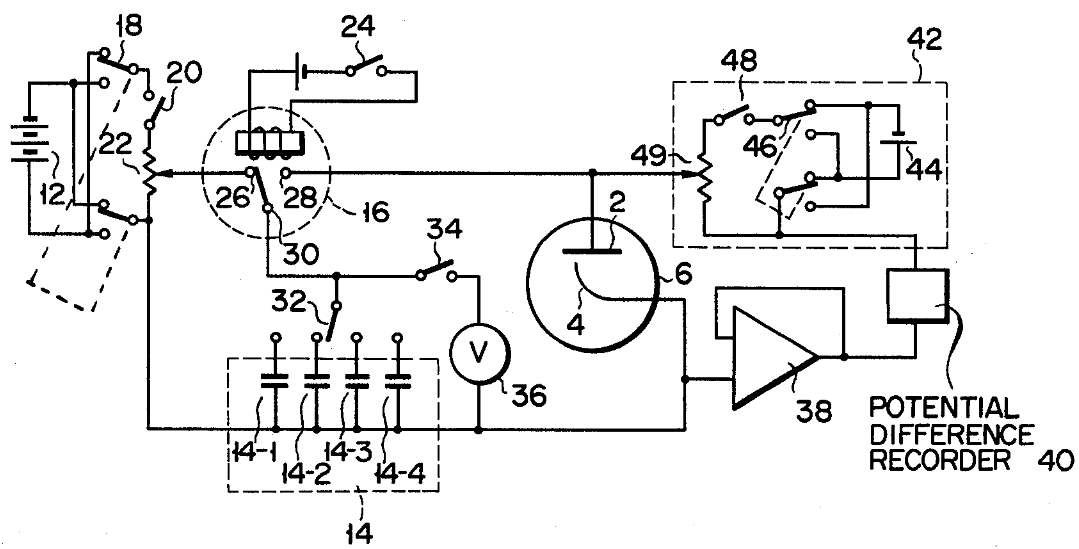
FIG. 3 is a circuit diagram of the measuring apparatus shown in FIG. 1.

Turning now to FIG. 3, there is shown a measuring apparatus for the method of evaluating the corrosion rate of a metal according to the invention. In the figure, the pulse generator 8 connected to the test metal piece 2 and the reference electrode 4 is comprised of a power source 12, a circuit 14 including a group of capacitors 14-1 to 14-4 for storing charge fed from the power source 12, and a relay 16 permitting the charge in the capacitor 14 to instantaneously discharge into the electric double layer of the test piece 2. The power source 12 is connected to a variable resistor 22 through a polarity reversal switch 18 and a power switch 20. The relay 16 is provided with a trigger switch 24, a normally closed contact 26 connected to a movable contact of the variable resistor 22, and a normally open contact 28 connected to the metal piece 2. A movable contact 30 of the relay 16 is connected to the fixed terminal of the variable resistor 22 through a rotary switch 32 and the capacitor 14, and to the reference electrode 4. The rotary switch 32 is used for the respective capacitors 14-1 to 14-4 with different capacitances $C_{14\text{-}1}$ to $C_{14\text{-}4}$ for selecting a desired one of them. The series circuit of the capacitor 14 and the rotary switch 32 is connected in parallel with the series circuit of switch 34 and voltmeter 36. It is necessary that the capacitance $C_{14\text{-}1}$ and $C_{14\text{-}r}$ of the capacitors 14-1 to 14-4 be not more than about 1/100, a small value sufficiently smaller than the capacitance $S.C_D$ of the test piece 2 as represented by the product of the differential capacitance $C_D$ and the area S of the test piece 2.

A potential measuring system for the working electrode 2, i.e. the metal piece, is comprised of an operational amplifier 38 as a voltage follower, the potential recorder 40, and a bias means 42. These are connected in series between the working electrode 2 and the reference electrode 4. The bias means 42 is comprised of a power source 44, a polarity reversal switch 46, an input switch 48, and a variable resistor 49. The movable contact of the variable resistor 49 is connected to the test metal piece 2 and the fixed terminal of the variable resistor 49 is connected to the potential recorder 40. The bias means 42 serves to bias the signal fed from the cell 6 so that the recorder 40 records the potential in a given measuring range. In other words, it is used for deleting the open circuit potential $E_{corr}$ of the metal piece 2 from the output signal.

In operation, the area S of the metal piece 2 in corrosion solution is measured and the open circuit potential of the metal piece 2 is recorded by the potential recorder 40. Then, the rotary switch 32 is rotated to select a desired capacitor 14-2, for example, and the power switch 20 is closed so that the capacitor 14-2 is charged through the path of the variable resistor 22, the relay 16, and the rotary switch 32. The amount of charge stored in the capacitor 14-2 can be readily calculated by turning on switch 34 to obtain the potential difference of the capacitor 14-2 across voltmeter 36.

Following this, when the start switch 24 is turned on, the relay 16 is operated so that the movable contact 30 is turned from the normally closed contact 26 to the normally open contact 28. At this time, charge stored in the capacitor 14-2 is instantaneously discharged into the double layer of the metal piece 2 through the reference electrode 4. When the start switch is opened, the movable contact 30 is immediately returned to the normally closed contact 26.

The charge q stored in the electrical double layer of the metal piece 2 is gradually consumed by the corrosion reaction of the metal piece 2 in the cell 6. Because the value of the capacitance $C_{14\text{-}2}$ of the capacitor 14-2 is selected to be not more than about 1/100 of the value of the capacitance $S.C_D$ of the test piece 2, most of the charge q contained in the capacitor 14-2 is instantly transferred to the test piece.

Figure 4:
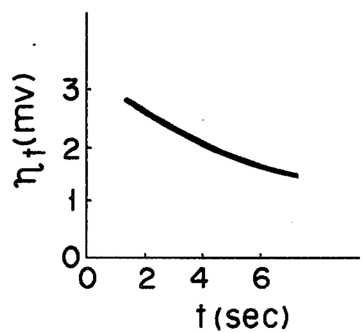
FIG. 4 shows a graph illustrating the relation of the polarization potential $\eta_t$ versus time.
Figure 5:
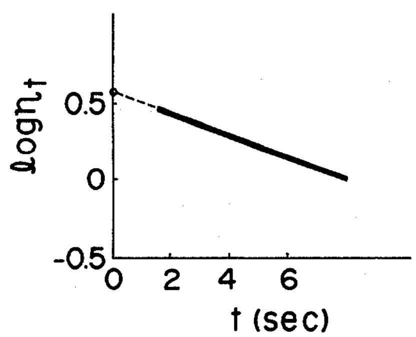
FIG. 5 is a graph illustrating the relationship between the logarithm of the polarization potential log $\eta_t$ and time t.

The potential $E_t$ of the test piece 2 gradually decays with time. The potential signal $E_t$ of the metal piece 2 is amplified by the operational amplifier 38 and recorded by the recorder 40. The polarization potential $\eta_t$ is calculated from the relation $\eta_t = E_t - E_{corr}$ and the variation thereof with time is recorded as shown in FIG. 4. The polarization potential $\eta_t$ is directly recorded by the recorder 10 since the bias potential $E_{corr}$ is applied to the metal piece 2. The measured values of the polarization potential $\eta_t$ are linearly plotted on the logarithmic graph as shown in FIG. 5. Therefore, the initial polarization potential $\eta_0$ may easily be obtained by extrapolation of such a graph to t = 0. By using the initial polarization potential $\eta_0$ and the charge density $\Delta q = q/S$ and the equations (4) and (5), the differential capacitance $C_D$ and the polarization resistance $R_p$ are calculated. From the equations (6) and (7), the corrosion rate V is obtained.

Figure 6:
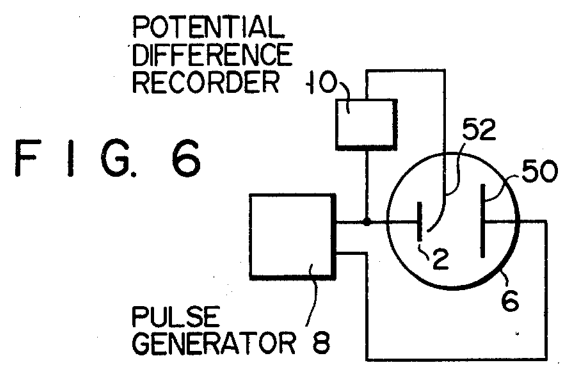
FIG. 6 illustrates in block form a measuring apparatus used for a method of evaluating the corrosion rate of a metal according to another embodiment of the present invention.
Figure 7:
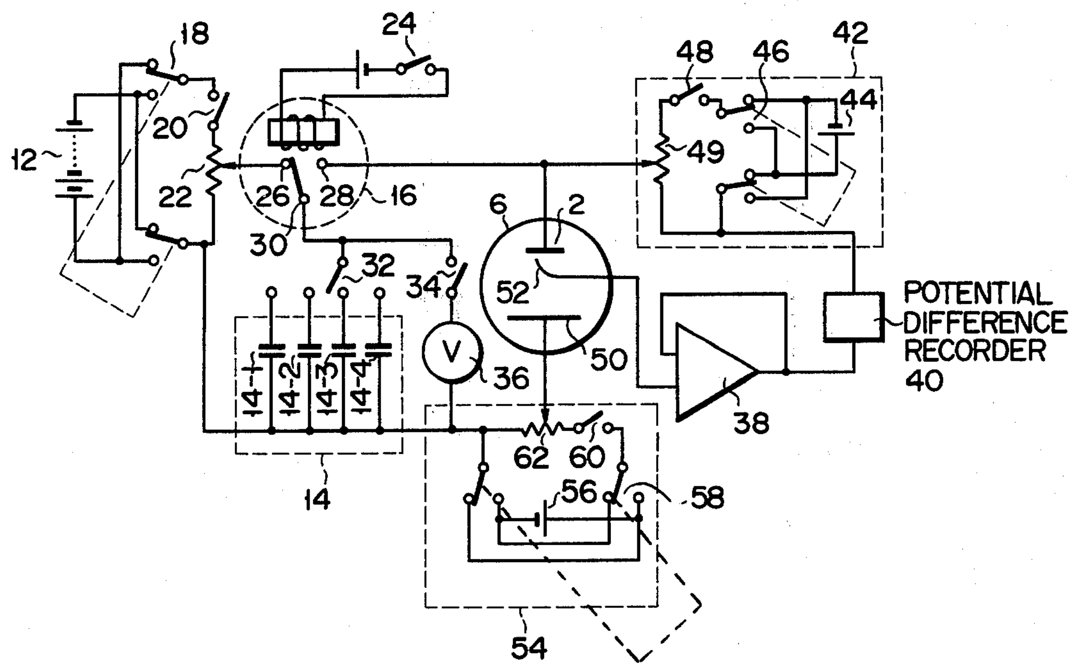
FIG. 7 shows a circuit diagram of the measuring apparatus shown in FIG. 6.

Referring now to FIGS. 6 and 7, there is shown another embodiment of the measuring apparatus for the method of evaluating the corrosion rate of a metal. In the figures, like reference numerals are used for designating like or equivalent portions in FIGS. 1 and 3.

As shown, a counter electrode 50 is provided in the cell of the measuring apparatus of this example. The additional electrode 50 is used for charging the electrical double layer of the test piece 2. In the previous example, the reference electrode 4 includes the function of the counter electrode 50 of the instant case. The reference electrode 52 is used merely as a reference electrode for measuring the potential of the test piece 2.

Because of the difference in electrode disposition, the circuit of FIG. 7 differs from that of FIG. 3, as a matter of course. Since the metal piece 2 is not charged through the reference electrode 52, the electrode 52 is not connected to the circuit 14. Because of the counter electrode 50, the bias means 54 is connected to the circuit 14. In the case when the test piece 2 and the counter electrode 50 have different natural potentials, the test piece 2, the counter electrode 50 and the test solution constitute a battery. Thus a potential difference occurs between the test piece 2 and the counter electrode 50. As a result, the electrical double layer of the test piece 2 may not be charged completely. To prevent such an insufficient charging, bias means 54 is arranged in the circuit to make equal the potentials of the test piece 2 and the counter electrode 50. The bias means 54 is comprised of a power source 56, a polarity exchange switch 58, input switch 60 and a variable resistor 62, the movable contact of which is connected to the counter electrode 50 and whose fixed terminal is connected to the circuit 14. The measuring apparatus of this example is operated in a manner similar to the previous example, for measuring the polarization potential.

Figure 8:
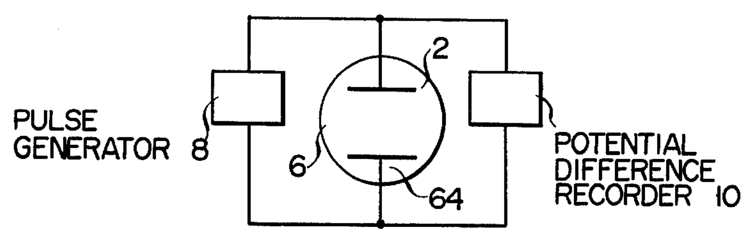
FIG. 8 illustrates in block form a measuring apparatus used for a method of evaluating the corrosion rate of a metal according to still another embodiment of the present invention.
Figure 9:
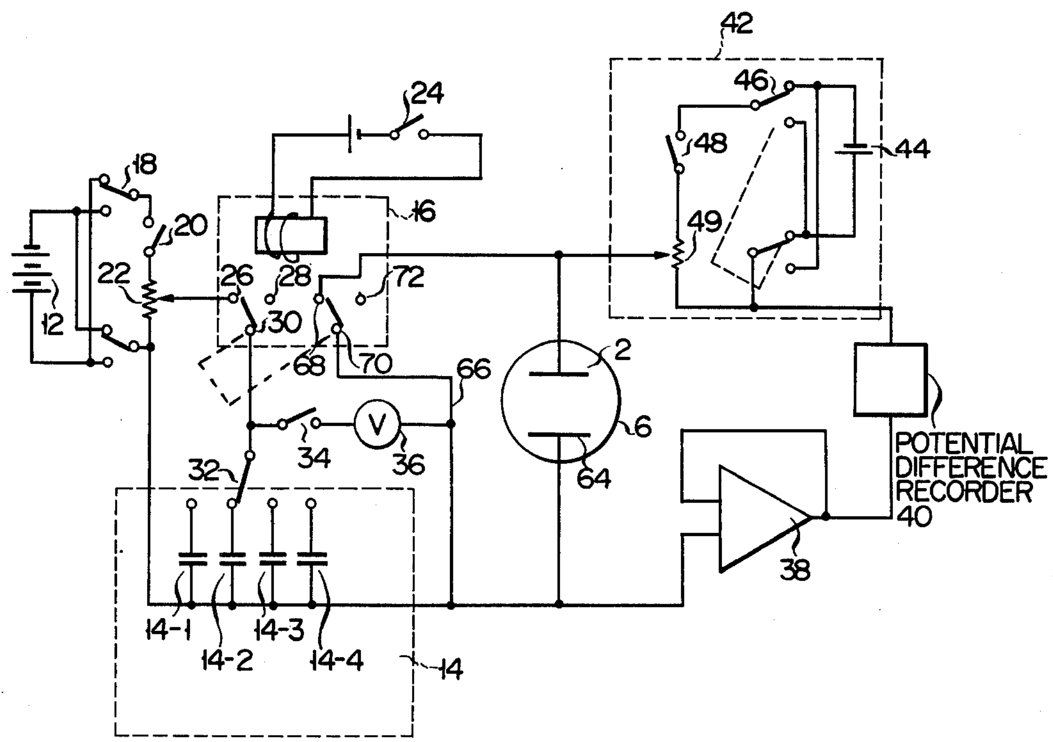
FIG. 9 shows a circuit diagram of the measuring apparatus shown in FIG. 8.

With reference to FIGS. 8 and 9 there will be explained still another measuring apparatus according to the invention. The apparatus shown in FIG. 8 is the same as the apparatus of FIG. 1 in basic construction. It differs in that a counter electrode 64 is arranged in the cell 6 in place of the reference electrode 4 as shown in FIG. 1. Unlike the reference electrode 4 which is made of such a material whose potential is unchanged if charged by the pulse generator 8, the second metal piece 64 is made of the same material as the first metal test piece 2. For this reason, a corrosion reaction occurs on the second metal piece 64 as well as the first metal test piece 2. As a result, the potential difference $\delta$ between the first and second test pieces changing according to the corrosion reaction on both the first metal piece 2 and the second metal piece 64 is recorded by the potential recorder 10.

It will now be explained how the polarization resistance $R_p$ based on the recorded potential difference between the first and second test pieces $\delta$ may be obtained.

Extrapolation is applied as mentioned above, thereby obtaining an initial potential difference $\iota_0$ from the recorded value. Then, the differential capacitance $C_D$ is arrived at by the following equation (13) which resembles equation (5):

$$\delta_o = \frac{q}{C_D}\left(\frac{1}{S_1} + \frac{1}{S_2}\right) \tag{13}$$

Here, $S_1$ denotes the area of the first metal test piece 2, and $S_2$ the area of the second metal test piece 64. Based on the differential capacitance $C_D$ and the slope $(-1/C_DR_p)$ of the line in the semi-logarithmic graph which provides the extrapolation, the polarization resistance $R_p$ can be obtained.

Equation (13) is formulated in the following way. The charge q between the solution and the electrical double layer of the first test piece 2 has the opposite polarity to the charge q between the solution and the electrical double layer of the second test piece 64. Both charges q are of the same absolute value. Thus, the surface charge density $\Delta q_1$ of the first piece 2 and the surface charge density $\Delta q_2$ of the second piece 64 are represented by the following equations (14) and (15), respectively:

$$\Delta q_1 = q/S_1 \tag{14}$$

$$\Delta q_2 = -q/S_2 \tag{15}$$

As explained with reference to equation (3), the time-based change of polarization potential $\delta_{1t}$ due to the corrosion reaction on the first metal test piece 2 and the time-based change of polarization potential $\delta_{2t}$ due to the corrosion reaction on the second metal test piece 64 are expressed by the following equations (16) and (17), respectively:

$$\delta_{1t} = \delta_{o1}\exp\left(-\frac{t}{C_DR_p}\right) \tag{16}$$

-continued $$\delta_{2t} = \delta_{o2}\exp\left(-\frac{t}{C_D R_p}\right). \quad (17)$$

In equations (16) and (17), $\delta_{o1}$ denotes the initial polarization potential of the first test piece 2, and $\delta_{o2}$ the initial polarization potential of the second test piece 64. In theory, these initial polarization potentials can be represented by the following equations:

$$\delta_{o1} = \frac{\Delta q_1}{C_D} = \frac{q}{S_1 C_D} \quad (18)$$

$$\delta_{o2} = \frac{\Delta q_2}{C_D} = \frac{-q}{S_2 C_D}. \quad (19)$$

Consequently, equation (16) and (17) are transformed as follows:

$$\delta_{1t} = \left(\frac{q}{S_1 C_D}\right)\exp\left(-\frac{t}{C_D R_p}\right) \quad (20)$$

$$\delta_{2t} = \left(\frac{-q}{S_2 C_D}\right)\exp\left(-\frac{t}{C_D R_p}\right). \quad (21)$$

Since the difference between $\delta_{1t}$ and $\delta_{2t}$ is recorded by the potential recorder 10, the potential difference $\delta$recorded by the recorder 10 is expressed as follows:

$$\delta = \delta_{1t} - \delta_{2t} = \frac{q}{C_D}\left(\frac{1}{S_1} + \frac{1}{S_2}\right)\exp\left(-\frac{t}{C_D R_p}\right) \quad (22)$$

Here, equation (22) is transformed into equation (13):

$$\delta_o = \frac{q}{C_D}\left(\frac{1}{S_1} + \frac{1}{S_2}\right) \quad (13)$$

If $S_1$ and $A_2$ are equal, that is $S_1 = S_2 = S$, equation (13) is transformed into equation (14):

$$C_D = \frac{\Delta q}{2\delta_o} \quad (23)$$

Thus, differential capacitance $C_D$ can easily be obtained by equation (13 ) or (23), just as easily as by equation (5).

The circuit shown in FIG. 9 is substantially the same as that shown in FIG. 3. It differs only in that a short circuit 66 is provided in order to equalize the open circuit potential of the first metal test piece 2 and that of the second metal test piece 64. The short circuit 66 has a normally closed contact 68, which is opened by the relay 16. Through the contact 68 and a movable contact 70, the first test piece 2 and the second test piece 64 are short-circuited with each other while the switch 24 remains open. When the switch 24 is closed, the movable contact 30 comes into contact with the normally opened contact 28. Upon contact between the contacts 28 and 30, the movable contact 70 contacts normally opened contact 68. As a result, short circuit 66 is opened.

The other constructional and functional aspects of the apparatus of the apparatus shown in FIGS. 8 and 9 are the same as those of the aforementioned embodiments.

Results cutured with the above-described embodiments the measuring apparatuses will be given below, compared to these obtained by the conventional methods.

(1) Measurement by the FIG. 3 measuring apparatus

Metal test piece (working electrode) — Pure copper plate

Solution — City water

Open circuit potential (corrosion potential) $E_{corr}$ — $-0.230\ V_{vs.}$ SCE

Charge density $\Delta q$ — 0.12 $\mu c/cm^2$

Under this condition, 3.4 mV was the initial polarization potential obtained by extrapolation of the of the measured date. The differential capacitance $C_D$ was 35 $\mu F/cm^2$. As as result, the following values were obtained.

Polarization resistance $R_p = 213\ K\Omega \cdot cm^2$

Corrosion rate $V = 0.27$ mdd

These values are fairly approximate to the polarization resistance $R_P = 215\ \Omega \cdot cm^2$ obtained by the constant current method and the corrosion rate $V = 0.266$ mdd by the weight loss method. This indicates that measurement by the apparatus of the invention is very accurate.

(2) Measurement by the FIG. 7 measuring apparatus

Test piece — Mild steel (SS-41)

Solution — City water

Open circuit potential $E_{corr}$ — $-0.653\ V_{vs}$·SCE

Charge density $\Delta q$ — 0.3 $\mu/cm^2$

Under this condition, the initial polarization potential $\eta_O$ was 4.3 mV by extrapolation of the measured data. The differential capacitance $C_D$ was 71 $\mu F/cm^2$. This results in the following muasured values.

Polarization resistance $R_p$ — 2.3 $\Omega \cdot cm^2$

Corrosion rate — 26 mdd

These values are fairly approximate to $R_P = 2.3\ \Omega \cdot cm^2$ obtained by the constant current method and the corrosion rate $V = 26.5$ mdd by the weight loss method. A high accuracy of measurement is proven.

From the foregoing description, it will be seen that the method of evaluating the corrosion rate of a metal according to the invention rapidly and accurately promides the polarization resistance $R_p$ and the corrosion rate V without any correction of the measured values.

What we claim is:

1. A method of evaluating the corrosion rate of metal in corrosive solution comprising:

feeding a given amount of charge q to the electrical double layer of a metal test piece having a given area S disposed in corrosive solution, said metal test piece being corroded to emit metal ions in the corrosion solution;

measuring the amount of polarization potential $\eta_t$ of said metal test piece, the amount of which potential sharply increases due to the application of the given amount of charge and which gradually decays due to the corrosion reaction back to the open circuit electrode potential measured versus a reference electrode disposed with said test metal piece in said corrosive solution, said amount of polarization potential being measured as a function of time;

calculating the initial polarization potential $\eta_0$ at time $t = 0$ after the cessation of said charge feeding from a plot of said polarization potential $\eta_t$ measured as a function of time, and deriving the polarization resistance $R_p$ which is inversely proportional to the corrosion rate from said initial amount of polarization potential $\eta_0$ and the charge q fed to said metal test piece;

whereby the corrosion rate of the metal is calculated by means of said polarization resistance $R_p$.

2. An evaluation method according to claim 1, in which said initial amount of polarization potential $\eta_0$ is obtained by extrapolating the plot of the variation of the amount of polarization potential $\eta_t$ as a function of time.

3. An evaluation method according to claim 1, in which said polarization resistance $R_p$ is calculated from the differential capacitance $C_D$ of the electrical double layer of said metal piece which is obtained from the charge density $\Delta q = q/S$ of the charge fed to said metal piece per unit area S and said initial amount of polarization potential obtained from said plot of polarization potential variation as a function of time.

4. An evaluation method according to claim 3, in which said initial amount of polarization potential $\eta_0$, said charge density $\Delta q$ and said differential capacitance $C_D$ are related by the equation $C_D = \Delta q/\eta_0$, and said polarization resistance $R_p$ is expressed by the slope of the plot of the logarithmic function $\log \eta_t$ versus time.

5. An evaluation method according to claim 4, in which said logarithmic function $\log \eta_t$ is given $$\log \eta_t = -t/R_pC_D + \log \eta_0.$$

6. An evaluation method according to claim 1, in which said corrosion rate of metal V is given $$V = (m/ZF) \cdot (K/2.3)/R_p$$

where K is a quotient obtained by dividing the product of the Tafel slopes of the anodic and cathodic reactions by the sum of said Tafel slopes, M is the atomic weight of said test piece, Z is the valence of the dissolved metal ion, and F is the Faraday constant.

* * * * *